Sept. 23, 1941. J. M. GOOD Plant Pat. 490
CHRYSANTHEMUM PLANT
Filed Feb. 11, 1941
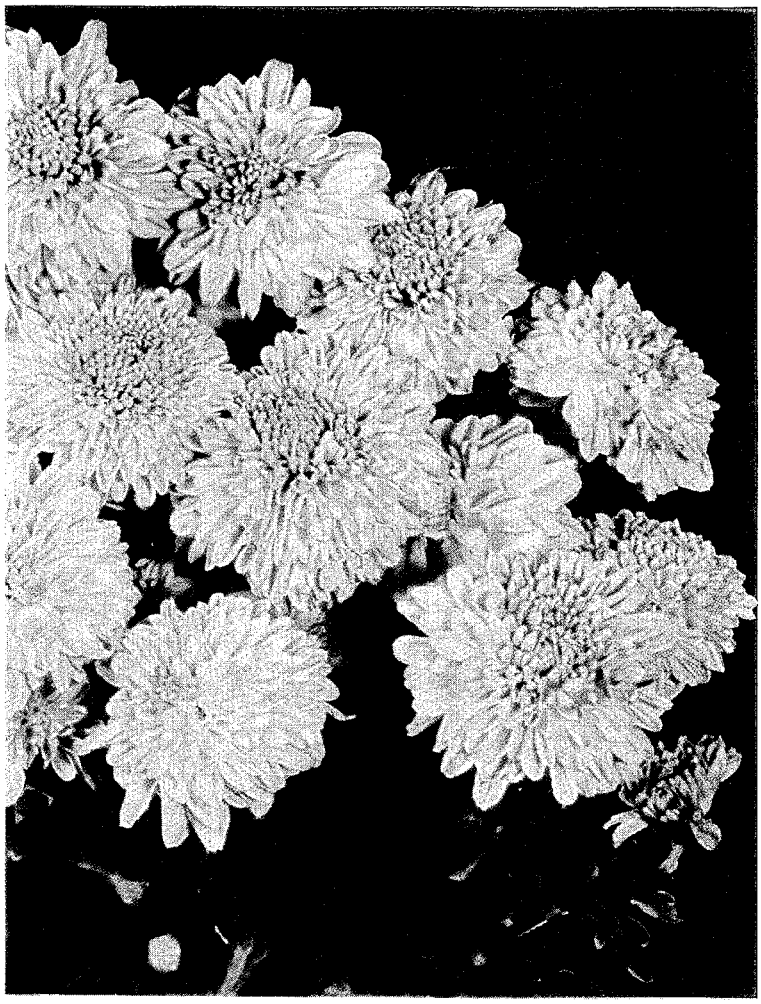
John M. Good Inventor
By Staley & Welch
Attorneys Patented Sept. 23, 1941

Plant Pat. 490

UNITED STATES PATENT OFFICE

490

CHRYSANTHEMUM PLANT

John M. Good, Springfield, Ohio, assignor to Good & Reece, Inc., Springfield, Ohio, a corporation of Ohio Application February 11, 1941, Serial No. 378,398

1 Claim. (Cl. 47—60)

This invention relates to a distinct and new variety of chrysanthemum plants, asexually reproduced, it particularly relating to a selection from a cross between the mum varieties "White Wings" (pistillate parent) and the "Aladdin" variety.

One of the features of this plant is its profuse and even blooming qualities, and its outstanding value as an outdoor cut flower. Another feature of the plant is its iron-clad hardiness, ease of culture, vigorous growth habit and earliness of blooming. Another feature relates to the color, the color plate references later referred to indicating Maerz and Paul's "A Dictionary of Color."

The accompanying illustration shows a cluster of fully open chrysanthemums of the new variety together with the stem and foliage.

*The plant.*—The plant has a vigorous, branching, upright type of growth, attaining a height of two to two and one half feet. The stems are rigid and long and are covered abundantly with medium-sized foliage very similar to the foliage of its pistillate parent. The plant stools freely, indicating its vigorous type of growth.

*The flower.*—Each stem bears large clusters of double flowers averaging 2–2½" in diameter. The color is a blend of Plate I—C—8 (Baby Pink) and Plate 42—D—I (Dawn) forming a color of Plate I—C—2 (Peachblossom). On first opening the center of the flower is colored with a very light yellow, which is lost as the flower fully opens, and matures. The individual blooms are borne on short, stiff peduncles, and are spaced so as to show off each individual bloom. All individual blooms are borne on a very even plane.

The petals are cupped at the edges forming a general boat-shape, especially at the ovary end.

As a cut flower it will last for at least two weeks with proper care. The color does not fade.

Since the flower is very double, most of the florets are ray florets with a small number of disk florets in the center.

Asexually the plant has come very true to form.

I claim:

A distinct and new variety of chrysanthemum plant as herein shown and described, characterized particularly by each stem bearing large clusters of double flowers with the color of each flower a blend of baby pink and dawn resulting in a color of peach blossom.

JOHN M. GOOD.